(12) United States Patent
Pan et al.

(10) Patent No.: US 8,996,581 B2
(45) Date of Patent: Mar. 31, 2015

(54) OBTAINING HIERARCHICAL INFORMATION OF PLANAR DATA

(75) Inventors: Yue Pan, Beijing (CN); Xing Zhi Sun, Beijing (CN); Ying Tao, Beijing (CN); Lin Hao Xu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 514 days.

(21) Appl. No.: 13/332,361

(22) Filed: Dec. 20, 2011

(65) Prior Publication Data

US 2012/0173585 A1 Jul. 5, 2012

(30) Foreign Application Priority Data

Dec. 30, 2010 (CN) .......................... 2010 1 0615062

(51) Int. Cl.
*G06F 7/00* (2006.01)
*G06F 17/30* (2006.01)
*G06Q 50/24* (2012.01)

(52) U.S. Cl.
CPC .......... *G06F 17/30592* (2013.01); *G06Q 50/24* (2013.01)
USPC ........................... 707/797; 707/793; 707/803

(58) Field of Classification Search
None
See application file for complete search history.

(56) References Cited

U.S. PATENT DOCUMENTS

| | | | |
|---|---|---|---|
| 7,016,910 B2 * | 3/2006 | Egilsson et al. ..................... 1/1 |
| 7,047,253 B1 * | 5/2006 | Murthy et al. ....................... 1/1 |
| 7,313,568 B2 | 12/2007 | Cutlip et al. .................. 707/102 |
| 7,493,253 B1 * | 2/2009 | Ceusters et al. ................... 704/9 |
| 7,539,591 B2 | 5/2009 | House et al. ................... 702/122 |
| 7,610,192 B1 * | 10/2009 | Jamieson ........................... 704/9 |
| 7,640,239 B2 | 12/2009 | Britton et al. ..................... 707/5 |
| 7,917,354 B2 * | 3/2011 | Ceusters et al. ................... 704/9 |
| 8,429,179 B1 * | 4/2013 | Mirhaji ......................... 707/756 |
| 8,458,191 B2 * | 6/2013 | Bhattacharjee et al. ...... 707/747 |
| 8,489,639 B2 * | 7/2013 | Yeh et al. ...................... 707/791 |
| 8,566,321 B2 * | 10/2013 | Majumdar ..................... 707/737 |

(Continued)

FOREIGN PATENT DOCUMENTS

| CN | 101470711 (A) | 7/2009 | ............. G06F 17/30 |
| CN | 101807194 (A) | 8/2010 | ............. G06F 17/30 |

OTHER PUBLICATIONS

Sundvall et al., "Integration of tools for binding archetypes to SNOMED CT," Oct. 27, 2008, pp. 1-10.*

(Continued)

*Primary Examiner* — Robert W. Beausoliel
*Assistant Examiner* — Hexing Liu
(74) *Attorney, Agent, or Firm* — Ido Tuchman; Jennifer R. Davis

(57) ABSTRACT

The invention provides a method and apparatus for obtaining hierarchical information of planar data. The method comprises mapping at least one data item from a same data set in the planar data to at least one node in a tree structure formed by a structured terminology system. The method also comprises obtaining at least one sub tree structure in the tree structure, each of the at least one sub tree structure taking the at least one node as all of its leaf node. The method also comprises selecting a target tree structure from the at least one sub tree structure and obtaining hierarchical information in the target tree structure. An apparatus corresponding to the above method is also provided. With the above method and apparatus, hierarchical information of data items may be obtained from planar organized data to facilitate subsequent and further analysis and management.

12 Claims, 6 Drawing Sheets

(56) References Cited

U.S. PATENT DOCUMENTS

| | | | |
|---|---|---|---|
| 8,645,904 B2* | 2/2014 | Coldicott et al. | 717/100 |
| 2005/0097628 A1* | 5/2005 | Lussier et al. | 800/260 |
| 2008/0046292 A1* | 2/2008 | Myers et al. | 705/3 |
| 2008/0126397 A1 | 5/2008 | Alexander et al. | 707/102 |
| 2009/0012928 A1* | 1/2009 | Lussier et al. | 706/59 |
| 2009/0024615 A1* | 1/2009 | Pedro et al. | 707/5 |
| 2009/0287670 A1* | 11/2009 | Hou et al. | 707/4 |
| 2010/0082651 A1* | 4/2010 | Akolkar et al. | 707/758 |
| 2010/0179951 A1 | 7/2010 | McPhail | 707/740 |
| 2010/0185652 A1* | 7/2010 | Bak et al. | 707/769 |
| 2010/0198612 A1* | 8/2010 | Streepy, Jr. | 705/2 |
| 2012/0029939 A1* | 2/2012 | Danielson et al. | 705/3 |
| 2012/0072235 A1* | 3/2012 | Varadarajan et al. | 705/3 |
| 2012/0179680 A1* | 7/2012 | Isaacson et al. | 707/737 |
| 2012/0215560 A1* | 8/2012 | Ofek et al. | 705/3 |
| 2012/0303608 A1* | 11/2012 | Wu et al. | 707/715 |
| 2012/0303668 A1* | 11/2012 | Srinivasan et al. | 707/792 |

OTHER PUBLICATIONS

Ruan et al., "An object-oriented design for automated navigation of semantic networks inside a medical data dictionary," 2000, Elsevier Science B.V, pp. 83-103.*

Lezcano et al., "Associating Clinical Archetypes Through UMLS Metathesaurus Term Clusters," May 29, 2010, Springer Science+Business Media, LLC 2010, pp. 1249-1258.*

Nadkarni et al., "Migrating existing clinical content from ICD-9 to SNOMED," May 30, 2010, pp. 602-607.*

Allones et al., "A study of semantic proximity between archetype terms based on SNOMED CT relationships," Department of Electronics and Computer Science, University of Santiago de Compostela, Spain, pp. 1-14.*

Yu et al., "An Investigation of Semantic Links to Archetypes in an External Clinical Terminology through the Construction of Terminological Shadows," Jan. 1, 2010, Dublin Institute of Technology, pp. 1-9.*

Xiaoyuan Wang et al., "SMDM: Enhancing EnterpriseWide Master Data Management Using Semantic Web Technologies", (pub date not know).

http://www.springerlink.com/content/u0882q0u676h40k3/, pp. 1-3, printed Oct. 19, 2010.

François-Paul Servant, "Linking Enterprise Data" LDOW2008, Beijing, China, pp. 1-5 (Apr. 22, 2008).

* cited by examiner

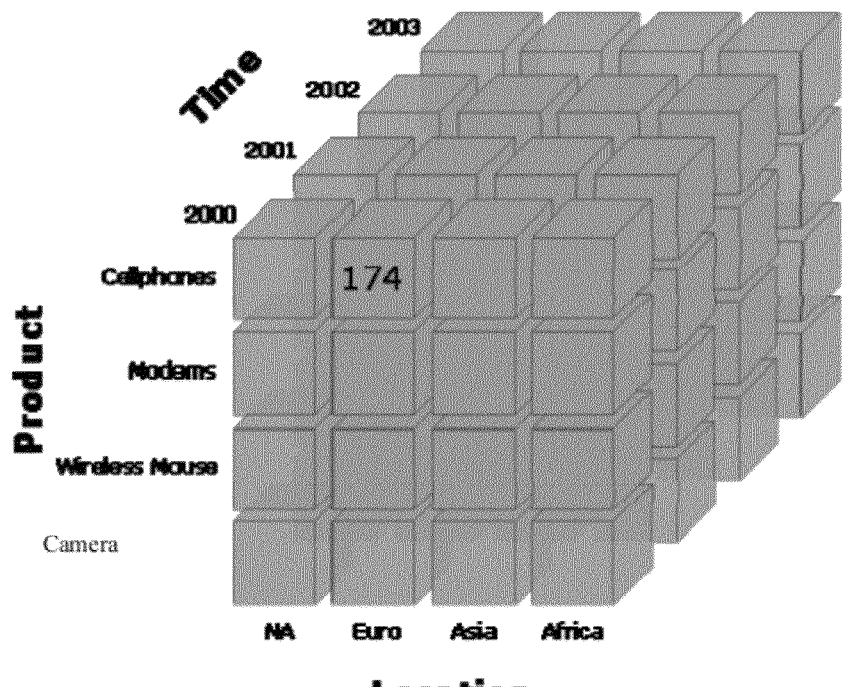

Fig. 1

| SSN | Main symptom | Fever | Smoke | Drink | X-ray | Diagnosis | Treatment | Outcome |
|---|---|---|---|---|---|---|---|---|
| 334210567 | cough | high fever | yes | yes | flakelike shade | branchitis | erythromycin | recovered |
| 557863421 | post-sternal severe pain | no | no | no | no | AMI | nitroglycerin | relieved |
| 985632456 | short of breath | no | yes | no | oval shade | small-cell lung cancer | cyclophosphamide | die |
| 327865556 | rusty sputum | remittent fever | yes | yes | flake-like shade | lobular pneumonia | cefradine | recovered |
| ... | ... | ... | ... | ... | ... | ... | ... | ... |
| 7832215643 | short of breath | no | yes | no | oval shade | adenoma of left lung | cyclophosphamide | relieved |

Fig. 2

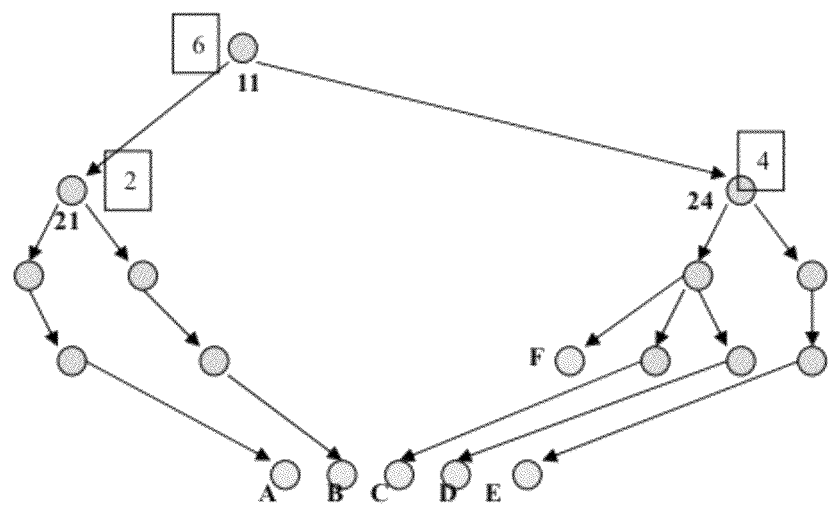
(1)
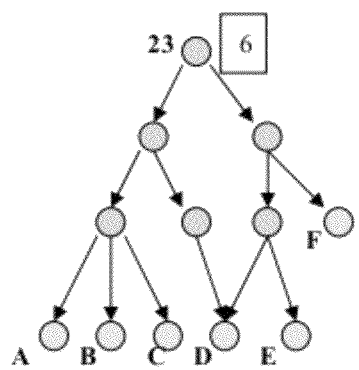
(2)
Fig. 4C

| level 0 | level 1 | level 2 | level 3 |
|---------|---------|---------|---------|
| 1 | 2 | 4 | A |
| 1 | 2 | 4 | B |
| 1 | 2 | 4 | C |
| 1 | 2 | 5 | D |
| 1 | 3 | 6 | E |
| 1 | 3 | F | F' |

OBTAINING HIERARCHICAL INFORMATION OF PLANAR DATA

CROSS-REFERENCE TO RELATED APPLICATIONS

This application claims priority under 35 U.S.C. §119 to Chinese Patent Application No. 201010615062.5 filed Dec. 30, 2010, the entire text of which is specifically incorporated by reference herein.

TECHNICAL FIELD OF THE INVENTION

The invention relates to the field of business intelligence, more particularly, to a method and apparatus for obtaining hierarchical information of planar data.

BACKGROUND

In recent years, Business Intelligence (BI) technology has provided the enterprise with comprehensive business data related service, such as performing data analysis, implementing data mining, creating data reports, revealing data laws, etc. By analyzing the data and deriving a report, it may help an enterprise to make more efficient business decisions. In Business Intelligence technology, dimensionalization and hierarchization of data is the basis for subsequent data analysis utilizing a cube model.

FIG. 1 shows an example of a cube model of multi-dimension and multi-hierarchy data. In this example, data related to product sale are organized into three dimensions along three axes, namely, time (x axis), location (y axis) and product (z axis), so as to depict function relationships between sales amount and time, location and product. Further, data of sales amount are structured into a plurality of hierarchies along each dimension, and thus, data analysis and management can be performed according to hierarchies. For example, on the dimension of location, the data of sales amount are structured into sales amount at each continent; for each continent, they may be further divided into sales amount at each country; for each country, they may in turn be divided into province, city and so on as needed. Similarly, for the dimension of time, they may be structured into year, quarter, month, day and so on as needed; for dimension of product, they may be further divided according to classification, series, model of product, etc. Based on these dimensionalized and hierarchized data, OLAP (On Line Analysis Process) analysis and operation may be performed on the data by using a cube model, so as to present integrated information from each dimension and hierarchy based on user needs.

It can be seen from the above example that dimensionalization and hierarchicalization of data have provided significant convenience for data modeling and analysis in business intelligence. In addition to typical hierarchized enterprise data, it is further desired to apply analysis and operation method in business intelligence on other data. However, in many fields, such as in clinical field, data are still organized and stored in "planar" manner. FIG. 2 shows an example of existing clinical data. In the example of FIG. 2, an electronic medical record, as a typical example of clinical data, includes various kinds of data such as main symptom of a patient, diagnostic conclusion, treatment, and etc. It can be seen that, all these data are listed in a planar form with fine granularity by using clinical terminology, without showing the association between data and hierarchical information of data, which are just the basis for cube modeling and OLAP operation in intelligent analysis. Many similar planar data also exists in other business data. Due to lack of hierarchical information, it is hard to perform further analysis and management on such data by using existing intelligent modeling and operation method, which brings limitation on systematization and intelligentization of data. Therefore, it is desired to perform processing on existing planar data to obtain its hierarchical information, so as to facilitate subsequent analysis and management on the planar data.

SUMMARY

The present invention is proposed in view of the above problems to obtain hierarchical information of planar data.

According to a first aspect of the invention, there is provided a method for obtaining hierarchical information of planar data. The method includes: mapping at least one data item from a same data set in the planar data to at least one node in a tree structure formed by a structured terminology system; obtaining at least one sub tree structure in the above tree structure, each of the at least one sub tree structure taking the at least one node as all of its leaf node; selecting a target tree structure from the at least one sub tree structure; and obtaining hierarchical information in the target tree structure.

According to a second aspect of the invention, there is provided an apparatus for obtaining hierarchical information of planar data. The apparatus includes: a node mapping unit configured to map at least one data item from a same data set in the planar data to at least one node in a tree structure formed by a structured terminology system; a sub structure obtaining unit configured to obtain at least one sub tree structure in the above tree structure, each of the at least one sub tree structure taking the at least one node as all of its leaf node; a target structure selecting unit configured to select a target tree structure from the at least one sub tree structure; and a hierarchical information obtaining unit configured to obtain hierarchical information in the target tree structure.

With the method and apparatus of the invention, hierarchical information between data items may be obtained from planar-organized data, so as to facilitate subsequently performing analysis and management on planar data.

BRIEF DESCRIPTION OF THE DRAWINGS

FIG. 1 shows an example of a cube model of multi-dimension and multi-hierarchy data.

FIG. 2 shows an example of existing clinical data.

FIG. 4B-4D show sub tree structures according to embodiments of the invention.

FIG. 4E shows an example hierarchy table corresponding to the tree structure in FIG. 4D.

DETAILED DESCRIPTION

Figure 3:
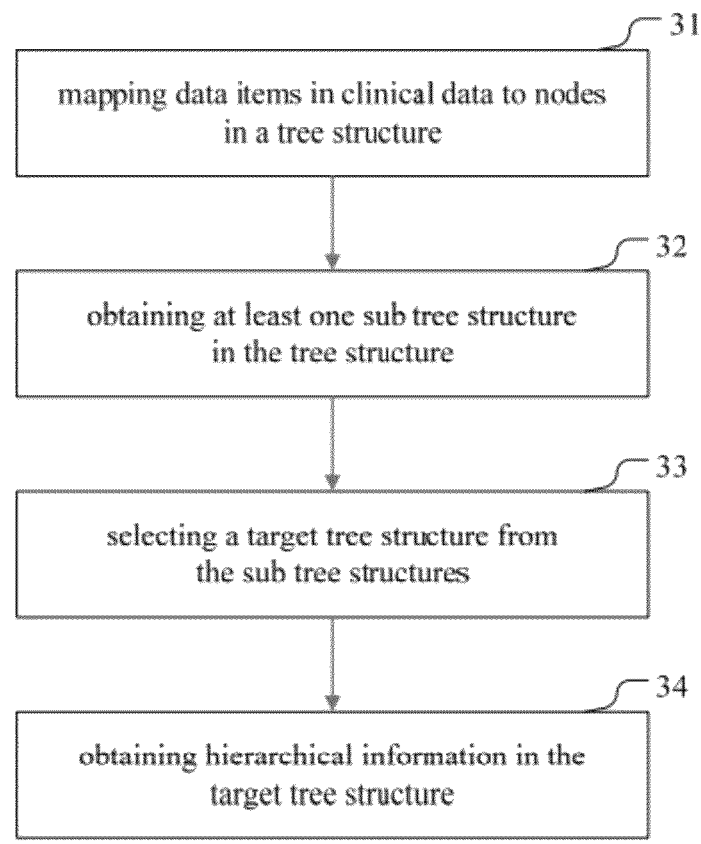
FIG. 3 shows a flowchart of a method according to embodiments of the invention.

Embodiments of the invention will be described in conjunction with detailed examples. It should be appreciated that the examples described for purpose of illustration should not be considered as a limitation to the substantial scope of the invention.

As stated above, the present invention provides such a method and apparatus as to obtain hierarchical information of planar data. However, such data per se contains only a plurality of data items organized in planar manner and cannot give relationships between each data item, and additionally, the plurality of data items usually are recorded in form of terminology in the field that the data belongs to. Thus, obtaining hierarchical information of planar data needs to have the aid of an external structured terminology system. Such structured terminology system should record normative terms in the field that the data belong to and organize these terms in hierarchical form, so as to indicate the classification and subordination relationship between various terms.

In the following, embodiments of the invention will be described by taking clinical data and structured terminology system in the clinical field for example.

As to selection of clinical terminology system, Systematized Nomenclature of Medicine (SNOMED) is a type of terminology system currently widely used, which provides a systematically organized computer processable collection of medical terminology covering most areas of clinical information such as diseases, findings, procedures, microorganisms, pharmaceuticals, etc. It allows a consistent way to index, store, retrieve, and aggregate clinical data across specialties and sites of care. It also helps organizing the content of medical records, reducing the difference among the way data is captured, encoded and used for clinical care of patients and for research.

In particular, SNOMED covers more than 365,000 clinical terms, and each term is specified by a unique numerical code, a unique name (namely, Fully Specified Name) and a "description". The above plurality of terms are organized into 19 upper level hierarchy structures including hierarchy of terms related to clinical procedure, hierarchy of terms related to drug, hierarchy of terms related to clinical disorder and the like. Each upper level hierarchy has several classified children hierarchies. For example, the drug-related terms may be classified based on the drug name, the dosage form, and etc, thus obtaining the further classified hierarchies. The clinical disorder-related terms may be classified based on the body sites, the causes, and etc., thus obtaining the further classified hierarchies. The different terms within a hierarchy or across hierarchies are linked by using about 1,460,000 "relationships". Thus, SNOMED forms a structured terminology system on the basis of description logic. In this terminology system, if only "subordination" relationships between terms are considered, a terminology relationship graph with a tree structure, in which each terminology is a node of the tree structure, can be obtained; and the connection line between nodes of the graph represents subordination relationship between nodes. Without losing generality, it can always be assumed that, there exists a most common concept to be used as root node of all terms. Usually, this root node is set as "Thing". Thus, all nodes are connected to the root node "Thing" as its child nodes. As stated above, since classification may be performed between terms from different perspectives, each node may have multiple child nodes and multiple parent nodes.

Based on the above features of SNOMED, it is a preferred selection to take SNOMED as the structured terminology system to depict hierarchy relationships between clinical terms. However, it is appreciated that, the selection of clinical terminology system is not limited only to SNOMED, but any normalized and structured terminology system, which has been already developed or will be developed in future, may be used, such as MedDRA terminology system. Such terminology systems may all form tree structure from different perspectives and different aspects, so as to express associations between nodes representing terms.

As to data in other fields such as data of biologic species, data in chemical field etc, there also exist corresponding structured terminology systems. As mentioned above, these structured terminology systems can organize standard terms in that field into tree structure form.

For purpose of detailed description, embodiments of the invention will be described below in conjunction with representative clinical data and SNOMED terminology system.

FIG. 3 shows a flowchart of a method according to embodiments of the invention. As shown in FIG. 3, the method for obtaining hierarchical information of planar data according to an embodiment of the invention comprises: step 31, in which at least one data item from a same data set in the planar data is mapped to at least one node in a tree structure formed by a structured terminology system; step 32, at least one sub tree structure in said tree structure is obtained, each of the at least one sub tree structure taking the at least one node as all of its leaf node; step 33, a target tree structure is selected from the at least one sub tree structure; and step 34, the hierarchical information of the target tree structure is obtained.

In particular, in step 31, data items in planar data may be located to a tree structure formed by the structured terminology system. To do this, firstly, a data set may be extracted from the planar data, and a plurality of data items in the data set are thus obtained, such that data items to be analyzed come from a same data set and reflect information from a same dimension. For example, in the clinical data shown in FIG. 2 that takes electronic medical record as an example, each vertical column may be regarded as a data set reflecting medical record information from one dimension. Specifically, each data item in the data set of the second vertical column is used to describe the main symptom of cases, each data item in the data set of the seventh vertical column is used to describe diagnosis conclusion of cases, and each data item in the data set of the eighth vertical column is used to describe treatment of cases. Therefore, data items that come from a same vertical column (that is, a same data set) need to be taken as objects to be analyzed by subsequent steps.

Next, for the obtained plurality of data items, each data item may be mapped to a term in the structured terminology system. In one embodiment, the planar data is clinical data, and the structured terminology system is the above mentioned SNOMED terminology system. Currently, many clinical data have already adopted the standard terminology in SNOMED terminology system to record clinical information, and some of them even directly adopt codes of terms in SNOMED terminology system to record and store data. In this case, mapping data items in clinical data to terms in SNOMED terminology system may be realized by simply performing search and match of terms or codes. In the case that clinical data are not recorded in normative terms, string match and fuzzy match between data items and terms may be additionally performed. In some embodiments, reference may also be made to the explanation or description of terms in the terminology system as assistance. For planar data of other contents, similarly, in cases where the planar data have been recorded with terms or codes in a structured terminology system, mapping of data items to terms may be directly realized by performing search and match on terms or codes. In cases where planar data are not recorded with normative terms, fuzzy match may be additionally performed. In addition, there are already many methods that are available for term matching in the art, and a person skilled in the art can choose an appropriate method on this basis to perform matching and mapping of data items and terms. Thus, each obtained data item may be mapped to a term in the structured terminology system.

Further, as mentioned above, since the structured terminology system organizes terms according to levels thereby forming a tree structure of terminology, the term corresponding to respective data item is taken as a node in the tree structure. Thus, data items are located into the tree structure.

Figure 4A:
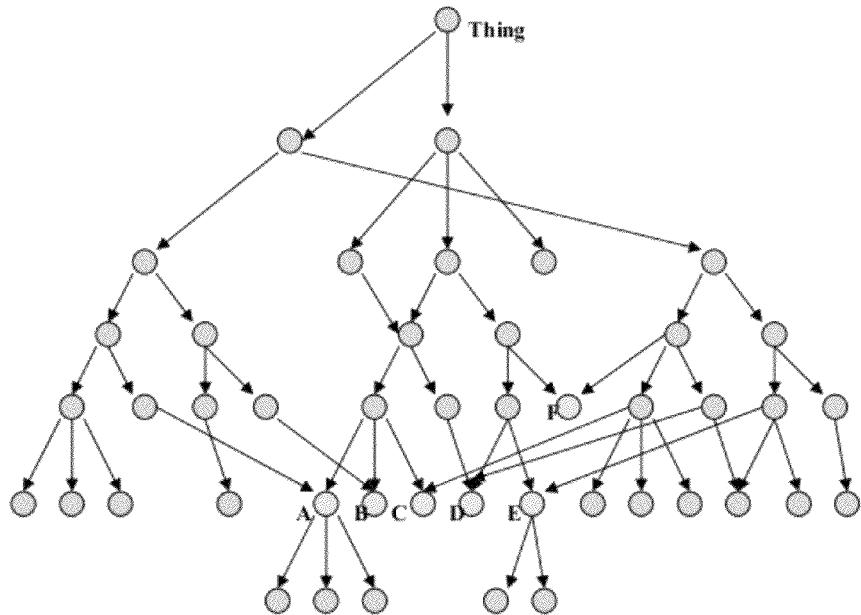
FIG. 4A shows a diagram of a tree structure according to an embodiment of the invention.

FIG. 4A shows a diagram of a tree structure according to an embodiment of the invention. The tree structure illustratively shows a portion of the tree structure formed by SNOMED terminology system, in which each node corresponds to one term, parent-child relationship between nodes are shown by connection line with arrow, and "Thing" is the root node of the entire tree structure. Through the mapping in the above step 31, data items are located to certain nodes in the tree structure. In FIG. 4A, nodes mapped from data items are shown by nodes A, B, C, D, E and F.

Next, the method of the embodiment proceeds to step 32, at least one sub tree structure which takes nodes mapped from data items as all of its leaf nodes is found in the above tree structure. Still referring to FIG. 4A, the process of step 32 is to find one or more sub tree structures in the entire tree structure, each of the sub tree structures taking nodes A-F as all of its leaf nodes.

To determine the candidate sub tree structure, connection relationships between nodes in the tree structure need to be utilized.

In one embodiment, a structured terminology system (such as SNOMED) that forms the tree structure is published in the form of linked open data (LOD). In this form, relationships between nodes in the tree structure are all described and stored in format of RDF triples. As is known to those skilled in the art, an RDF triple expresses various meaning and relationships in form of <subject, predicate, object>. Subordination relationship (or referred to as parent-child relationship) of node A and B may be represented as <nodeA, subClassOf, nodeB> with RDF triple. As a semantic-based language, in LOD data, there is a concept owl:Thing, and each individual item in the LOD data is a member thereof or is referred to as its child node. Accordingly, if it is desired to query a parent node of the node "childNode" in LOD, the following SPARQL query may be utilized: Select ?parentNode where {?parentNode rdfs:subClassOf <childNode>}, so as to obtain the value of the parent node. The child node of a given parent node may also be similarly queried. In this case, parent-child relationship between nodes may simply be obtained through the core predicate subClassOf. In other embodiments, the structured terminology system is stored in other specific formats. Accordingly, parent-child relationships between nodes in the tree structure may be obtained by capturing description on the subordination relationship in the other specific format.

On basis the that parent-child relationships between nodes can be obtained, traversing upward or downward may be performed in the tree structure, and a sub tree structure may thus be determined through such traversing.

In one embodiment, traversing downward is performed from root node Thing of the tree structure to determine paths and corresponding nodes that can arrive at leaf nodes A-F, and such paths and nodes are combined into a sub tree structure.

In one embodiment, traversing upward is performed from leaf nodes A-F till root node Thing. During this process, for each leaf node, at least one parent node of the leaf node may be identified by obtaining the nodes with "subClassOf" relationship through the above SPARQL query for example. Then starting from each parent node, the ancestor nodes with higher level may be obtained in turn till arriving at the root node Thing, thereby forming a single path from the leaf node to the root node. Thereafter, for the obtained multiple paths, common nodes between different paths may be found so as to merge the obtained paths, thereby obtaining a sub tree structure from the leaf node to the root node Thing.

Figure 4B:
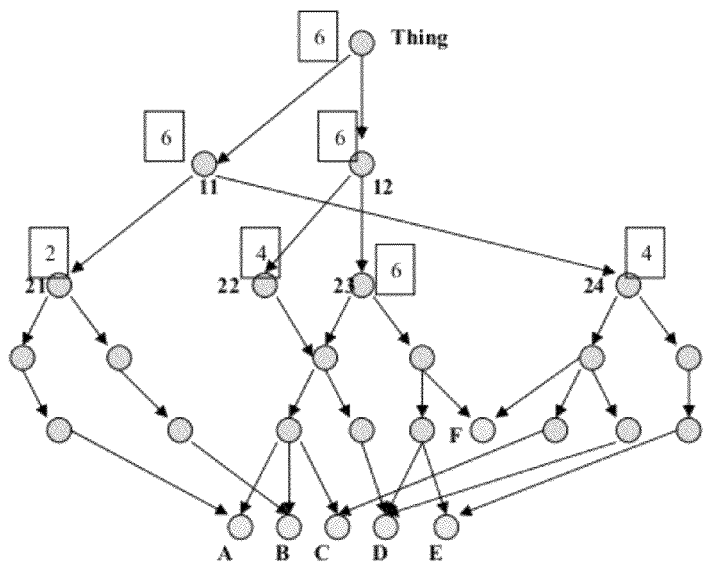

FIG. 4B shows a sub tree structure obtained from the tree structure in FIG. 4A according to an embodiment of the invention. As shown in FIG. 4B, the obtained sub tree structure is a portion of the tree structure of FIG. 4A. All leaf nodes of the sub tree structure are just nodes A-F mapped from data items, and the root node is still Thing. However, it may be found by observing this sub tree structure from the root node Thing to the leaf nodes A-F that the sub tree structure is not the only sub structure that takes nodes A-F as leaf nodes, but contains further sub tree structure, such as a further sub tree structure with node 11 as root node. That is, multiple sub tree structures may be determined by performing traversing between leaf nodes A-F and the ultimate root node Thing, and these sub tree structures can all reflect potential hierarchy relationships between nodes A-F from a certain perspective or aspect. Therefore, one of the obtained multiple sub tree structures may be determined as the target tree structure as needed, and the hierarchical information of nodes may be reflected by that target tree structure, as shown at step 33.

In one embodiment, to make finally obtained hierarchical information more relevant, the obtained multiple sub tree structures need to be further filtered, and the relatively "compact" tree structure will be selected therefrom to reflect the hierarchical information, since in a hierarchy tree with relatively "compact" structure, nodes have stronger association between them to better reflect specific classification and topic of the tree.

The above selection process will be described below in conjunction with an example of the sub tree structure shown in FIG. 4B.

In one embodiment, two steps are utilized to analyze and select from multiple sub tree structures. Firstly, for the sub tree structure from leaf nodes to the ultimate root node Thing shown in FIG. 4B (referred to herein as first sub tree structure), candidate root nodes are preliminarily selected. In particular, in the first sub tree structure, starting from the ultimate root node Thing, the number of leaf nodes that are reachable from the current node may be determined by traversing downward. If the number of leaf nodes that are reachable from the current node equals the number of all leaf nodes (in the example of FIG. 4A-4B, the number of all leaf nodes is 6), then the number of reachable leaf nodes from the child node of current node may be further judged until the number of reachable leaf nodes is smaller than the number of all leaf nodes. Then, the node of the first class may be taken as candidate root node, and the node of the second class may be removed. The node of the first class is characterized in that, the number of reachable leaf nodes equals the number of all leaf nodes, and the number of reachable leaf node of its child nodes are all smaller than number of all leaf nodes. The node of the second class is characterized in that, the number of the reachable leaf nodes of that node and at least one child node thereof both equal to the number of all leaf nodes. This is because, assume node m is the parent node of node n and all leaf nodes are reachable from these two nodes, that is, node m is the node of the second class, then the sub tree structure N taking node n as root node must be a subset of the sub tree structure M that takes node m as root node. Thus, compared with tree structure M, tree structure N will necessarily contain less levels and nodes, thereby being more compact. Therefore, the node of the second class may not be considered as the appropriate root node and might be removed.

In FIG. 4B, the number of reachable leaf nodes of some of the nodes are indicated with a solid line box. For example, the number of reachable leaf nodes of the root node Thing and its two child nodes 11 and 12 are 6, and additionally, the number of reachable leaf nodes of one child node 23 of node 12 is also 6. Thus, the root node Thing and node 12 are nodes of the second class and should be removed, and node 11 and node 23 should be taken as candidate root nodes. Thus, two candidate sub tree structures, as shown in FIG. 4C, are preliminarily selected from the first sub tree structure shown in figure 4B, the two sub tree structures taking node 11 and node 23 as root node respectively.

Next, further judgment may be performed on the preliminarily selected sub tree structures. In particular, the number of nodes contained in each sub tree structure may be determined and the sub tree structure with the least number of nodes therein may be selected as the target structure. In the two sub tree structures shown in FIG. 4C, structure (1) involves 18 nodes and structure (2) involves 12 nodes. Thus, structure (2) is more compact than structure (1), and the relevance between nodes in (2) is more than that in (1). Therefore, structure (2) should be selected as the target structure for reflecting hierarchical information between leaf nodes.

Although a more compact sub tree structure is selected as the target tree structure through two steps in the above, it is appreciated that other approaches may also be employed to analyze and select sub tree structures. For example, in one embodiment, for each potential sub tree structure, the number of nodes contained therein is directly determined and the sub tree structure with the least number of node is selected as the target tree structure. In another embodiment, a specific leaf node is selected first. Then for each potential sub tree structure, the length of the path from the root node to that specific leaf node, that is the number of levels, is determined, and the sub tree structure with less number of levels is selected as the target tree structure. This approach may be used to preliminarily filter sub tree structures, directly determine target tree structure, or determine final target tree structure in conjunction with judgment on the number of nodes.

With the above various methods, a relatively compact tree structure may be found as the target tree structure from a plurality of sub tree structures. Moreover, in one embodiment, the level where each leaf node is located in the target structure is further analyzed and adjusted to make the final hierarchical tree more symmetric and balanced in structure.

Figures 4D, 4E:
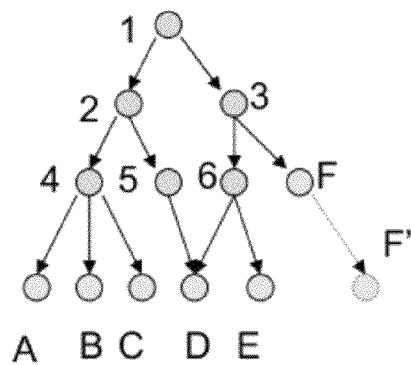

In particular, referring to structure (2) in FIG. 4C, structure (2) may be selected as the target tree structure due to its compactness. However, in this tree structure, although all being leaf nodes, node F and other leaf nodes A-E are not at the same level. In other words, path length from the root node to each leaf node is not the same. Thus, that tree structure is not a balanced tree structure. Since a balanced tree structure may be more beneficial to subsequent hierarchical information analysis, the target tree structure may be adjusted to make it "balanced". In one example, for node F at a higher level, that is, the node whose distance to the root node is shorter than other leaf nodes, a dummy child node F' is set, which has the same content with node F, but is located at the level same as other leaf nodes A-E, as shown in FIG. 4D. Thus, all leaf nodes in the adjusted tree structure are at the same level, thereby realizing balance in structure. It is appreciated that, if there is more than one level difference between leaf nodes, it may require setting dummy child nodes of two or more levels for the leaf node at higher level, so as to finally make all leaf nodes in target tree structure at same level.

In summary, through the above method, a compact and balanced target tree structure can be obtained that takes nodes mapped from data items as leaf nodes. Based on this, at step 34, the hierarchical information between nodes may be obtained from the target tree structure, and thus the association between data items corresponding to leaf nodes may be learned. For example, through the target tree structure shown in FIG. 4D, the hierarchical information between leaf nodes A-F may be obtained, and thus the inherent relationship between clinical data items corresponded to leaf nodes A-F may be obtained. For example, data items corresponding to leaf nodes A-C belong to a same classification (the term corresponding to node 4), data items corresponding to leaf nodes D, E belong to a same classification (the term corresponding to node 5), and so on.

In one embodiment, in step 34, the hierarchical information may also be extracted from the obtained target tree structure by way of tabulation. For example, for the target tree structure shown in FIG. 4D, a hierarchy table corresponding to the tree structure may be obtained by placing respective nodes into corresponding levels along paths from the root node to the leaf nodes. FIG. 4E shows a hierarchy table corresponding to the tree structure in FIG. 4D. In other embodiments, the hierarchical information may also be organized into other forms.

Based on the above obtained hierarchical information, it is possible to perform OLAP analysis and operation widely adopted in business intelligence on planar organized data items, thereby revealing inherent association and data rules from discrete and planar data items, so as to perform better analysis and management on information.

Figure 5:
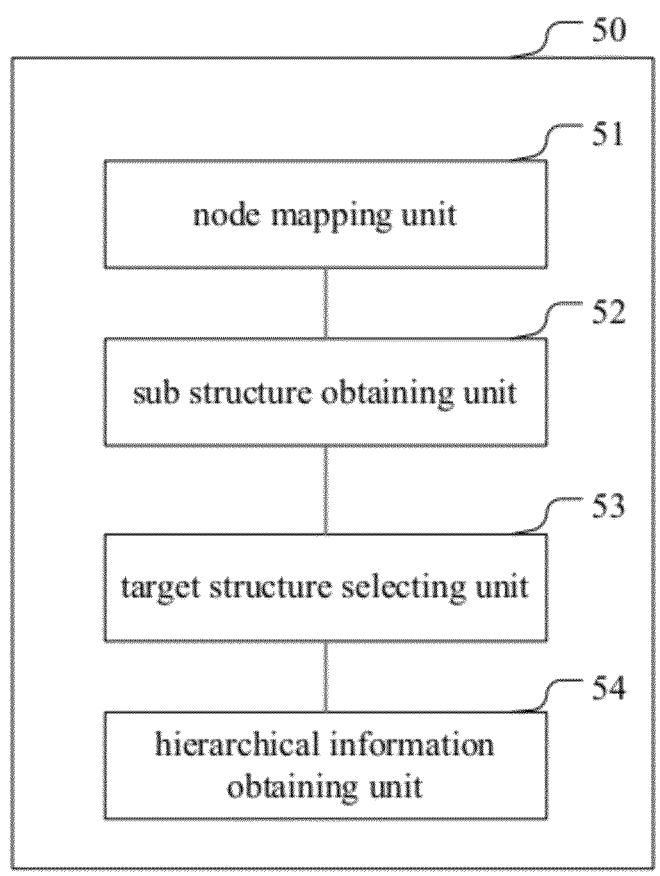
FIG. 5 shows a block diagram of an apparatus according to an embodiment of the invention.

Based on the same inventive conception, the present invention also provides an apparatus for obtaining hierarchical information of planar data. FIG. 5 shows a block diagram of an apparatus according to an embodiment of the invention. As shown in FIG. 5, the apparatus 50 of the embodiment of the invention comprises: a node mapping unit 51 that may be configured to map at least one data item from a same data set in the planar data to at least one node in a tree structure formed by a structured terminology system; a sub structure obtaining unit 52 that may be configured to obtain at least one sub tree structure from the above tree structure, each of the at least one sub tree structure taking said at least one node as all of its leaf nodes; a target structure selecting unit 53 that may be configured to select a target tree structure from the at least one sub tree structure; and a hierarchical information obtaining unit 54 that may be configured to obtain the hierarchical information in the target tree structure.

In particular, the node mapping unit 51 may be used to locate data items in planar data to a tree structure formed by the structured terminology system. To do this, firstly, the node mapping unit 51 may extract a data set from the planar data and obtains a plurality of data items in the data set, such that data items to be analyzed come from a same data set and reflect information of a same dimension. Next, for the obtained plurality of data items, the node mapping unit 51 may map each data item to a term in the structured terminology system. In the case where the planar data have been described with normative terms in the structured terminology system, the node mapping unit 51 may realize the mapping of data items to terms by simply performing search and match on terms or codes. In the case where planar data are not recorded with normative terms, the node mapping unit 51 may additionally perform string match and fuzzy match between data items and terms, thereby mapping data items to terms. Further, since the structured terminology system organizes terms according to levels thereby forming a tree structure of terminology in which one term is one node of that tree structure, when the node mapping unit 51 maps data items to terms, the data items may be mapped to nodes in the tree structure at the same time.

Next, the sub structure obtaining unit 52 may find at least one sub tree structure which takes nodes mapped from data items as all of its leaf nodes in the above tree structure.

To obtain candidate sub tree structure, the sub structure obtaining unit 52 may utilize the description on connection relationship (especially parent-child relationship) between nodes in various formats for recording and storing the structured terminology system. If parent-child relationships between nodes can be obtained, the sub structure obtaining unit 52 may traverse upward or downward in the tree structure, and determine sub tree structures through such traversing.

In one embodiment, the sub structure obtaining unit 52 traverses downward from root node Thing of the tree structure to determine the paths that can arrive at respective leaf nodes, wherein the leaf nodes are nodes mapped from data items by the node mapping unit 51. The sub structure obtaining unit 51 may combine such paths with nodes involved therein as a sub tree structure. In another embodiment, the sub structure obtaining unit 52 traverses upward from the leaf nodes till the root node Thing, thereby forming paths from the leaf nodes to the root node. Thereafter, for the obtained multiple paths, common nodes between different paths may be found so as to merge the obtained paths, thereby obtaining a first sub tree structure from the leaf nodes to the root node Thing. Generally, the first sub tree structure actually contains many possible sub tree structures, so the obtained multiple sub tree structures may be further filtered as needed to select an appropriate sub tree structure therefrom as target tree structure, so as to reflect hierarchical information.

Then, the target structure selecting unit 53 may analyze the multiple sub tree structures obtained by the sub structure obtaining unit 52 and may select a target tree structure therefrom that can reflect hierarchical information of nodes.

In one embodiment, the target structure selecting unit 53 utilizes two steps to analyze multiple sub tree structures and selects a more compact sub tree structure as the target tree structure. Firstly, in the first sub tree structure, the number of reachable leaf nodes for each node may be determined by traversing downward starting from the ultimate root node Thing. Then, a node of the first class may be taken as the candidate root node and a node of the second class is removed. The node of the first class is characterized in that, the number of reachable leaf node equals the number of all leaf nodes, and the number of reachable leaf nodes of the child nodes of the node of the first class is all smaller than the number of all leaf nodes. The node of the second class is characterized in that, the number of reachable leaf nodes of the node of the second class and at least one child node thereof all equals to the number of all leaf nodes.

Next, judgment may be further performed on preliminarily selected sub tree structures from which the node of the second class has been removed. In particular, the target structure selecting unit 53 may determine the number of nodes contained in each sub tree structure and may select the sub tree structure with the least number of nodes therein as the target structure.

Through the above respective units, the apparatus 50 may obtain multiple sub tree structures that take nodes mapped from data items as leaf nodes and find a more compact tree structure therefrom as the target structure. Further, in one embodiment, the apparatus 50 also comprises a balancing unit (not shown) that may be configured to analyze and adjust the levels where leaf nodes are located in the target structure to make the final target structure more symmetric and balanced. In particular, if the respective leaf nodes in the target structure locate at different levels, the balancing unit may balance the target structure by setting dummy child nodes, such that all leaf nodes in the target tree structure are at the same level.

On the basis that target tree structure is determined, the hierarchical information obtaining unit 54 may extract the hierarchical information from the target tree structure, thereby displaying the association between respective nodes, and further, displaying hierarchical information between data items corresponding to respective nodes.

The detailed examples that the apparatus 50 according to embodiments of the invention obtains hierarchical information of planar data are similar to that of the above method and details of which will be omitted here for brevity.

With the method and apparatus of various embodiments, hierarchical information of planar data may be obtained by means of structured terminology system, so as to facilitate subsequent analysis and management on planar data.

It may be appreciated by a person skilled in the art that, the above method and apparatus for obtaining hierarchical information of planar data can be implemented by using computer executable instructions and/or included in processor control codes, which are provided on carrier medium such as disk, CD or DVD-ROM, programmable memory such as read-only memory or data carrier such as optical or electrical signal carrier. The apparatus of the present embodiment and its components can be implemented by hardware circuit such as large scale integrated circuit or gate arrays, semiconductors such as logic chip or transistors, or programmable hardware devices such as field programmable gate array, programmable logic device, or can be implemented by software executed by various types of processors, or can be implemented by a combination of the above hardware circuit and software. Software and program code for carrying out operations of the present invention may be written in any combination of one or more programming languages, including, but not limited to, an object oriented programming language such as Java, Smalltalk, C++ or the like and conventional procedural programming languages, such as the "C" programming language or similar programming languages. The program code may be executed on a computer locally or remotely to accomplish intended operations.

Although the method and apparatus of the invention for obtaining hierarchical information of planar data have been described above in detail in conjunction with detailed embodiments, the invention is not limited thereto. Those skilled in the art can make various variations, replacements and alternations thereto under teaching of the invention without departing from the spirit and scope of the invention. It should be appreciated that, all such variations, replacements and alternations still fall within protection scope of the invention which is defined by appended claims.

The invention claimed is:

1. A method for obtaining hierarchical information of planar data, the method comprising:
    mapping at least one data item from a same data set in the planar data to at least one node in a full tree structure formed by a structured terminology system;
    obtaining at least one sub tree structure in the full tree structure, each of the at least one sub tree structure taking the at least one node as leaf nodes of the sub tree structure;
    selecting a target tree structure from the at least one sub tree structure;
    obtaining hierarchical information in the target tree structure;

determining a path length from a root node of the sub tree structure to a certain leaf node for each of the at least one sub tree structure; and selecting a sub tree structure with a path length shorter than at least one other determined path length as the target tree structure;

wherein the step of obtaining at least one sub tree structure in the full tree structure comprises:

taking a node of the first class as a candidate root node in the full tree structure, wherein the node of the first class is characterized in that, the number of leaf nodes of the full tree structure reachable from the node of the first class equals the number of all leaf nodes of the full tree structure, and the numbers of leaf nodes of the full tree structure reachable from each child node of the node of the first class are all smaller than the number of all leaf nodes of the full tree structure; and obtaining a sub tree structure, wherein the root node of the sub tree structure is the node of the first class; and wherein the step of obtaining at least one sub tree structure in the full tree structure further comprises:

traversing upward starting from each of the at least one node as a leaf node until a root node of the full tree structure, thereby forming at least one path from the leaf node to the root node of the full tree structure;

merging the at least one path to obtain a first sub tree structure from the leaf node to the root node of the full tree structure; and obtaining at least one sub tree structure of the first sub tree structure.

2. The method according to claim 1, wherein the step of mapping at least one data item to at least one node comprises: mapping the at least one data item to at least one terminology in the structured terminology system; and mapping the at least one terminology to the at least one node in the full tree structure.

3. The method according to claim 1, wherein the step of selecting a target tree structure comprises:

determining a number of nodes contained in each of the at least one sub tree structure, and selecting a sub tree structure having a least number of nodes as the target tree structure.

4. The method according to claim 1, further comprising: balancing the target tree structure by setting a dummy child node for a leaf node at a higher level, to cause all leaf nodes to be at a same level.

5. The method according to claim 1, wherein the step of obtaining the hierarchical information in the target tree structure comprises: extracting hierarchy relationships among nodes in the target tree structure and organizing the hierarchy relationship and the nodes in the target tree structure into a hierarchy table.

6. The method according to claim 1, wherein the planar data is clinical data that comprises an Electronic Medical Record, and the structured terminology system comprises a Systematized Nomenclature of Medicine (SNOMED) terminology system.

7. An apparatus for obtaining hierarchical information of planar data, the apparatus comprising:

a computer processor;

a memory storing instructions when executed by the computer processor to perform the following instructions:

mapping at least one data item from a same data set in the planar data to at least one node in a full tree structure formed by a structured terminology system;

obtaining at least one sub tree structure in the full tree structure, each of the at least one sub tree structure taking the at least one node as leaf nodes of the sub tree structure;

selecting a target tree structure from the at least one sub tree structure; and obtaining hierarchical information in the target tree structure;

wherein the obtaining instruction is configured to:

take a node of a first class as a candidate root node in the full tree structure, wherein the node of the first class is characterized in that, the number of leaf nodes of the full tree structure reachable from the node of the first class equals the number of all leaf nodes of the full tree structure, and the numbers of leaf nodes of the full tree structure reachable of each child node of the node of the first class are all smaller than the number of all leaf nodes of the full tree structure; and obtain a sub tree structure, wherein a root node of the sub tree structure is the node of the first class;

wherein the selecting instruction is configured to:

determine a path length from the root node of the sub tree structure to a certain leaf node for each of the at least one sub tree structure; and select a sub tree structure with a path length shorter than at least one other determined path length as the target tree structure; and wherein the obtaining instruction is further configured to:

traverse upward starting from each of the at least one node as a leaf node until a root node of the full tree structure, thereby forming at least one path from the leaf node to the root node of the full tree structure;

merge the at least one path to obtain a first sub tree structure from the leaf node to the root node of the full tree structure; and obtain at least one sub tree structure of the first sub tree structure.

8. The apparatus according to claim 7, wherein the mapping instruction is configured to:

map the at least one data item to at least one terminology in the structured terminology system; and map the at least one terminology to the at least one node in the full tree structure.

9. The apparatus according to claim 7, wherein the selecting instruction is configured to:

determine a number of nodes contained in each of the at least one sub tree structure; and select a sub tree structure having a least number of nodes as the target tree structure.

10. The apparatus according to claim 7, further comprising a balancing instruction to: balance the target tree structure by setting a dummy child node for a leaf node at a higher level, to cause all leaf nodes to be at a same level.

11. The apparatus according to claim 7, wherein the obtaining instruction is configured to: extract hierarchy relationships among nodes in the target tree structure and organize the hierarchy relationships and the nodes in the target tree structure into a hierarchy table.

12. The apparatus according to claim 7, wherein the planar data is clinical data that comprises an Electronic Medical Record, and the structured terminology system comprises a Systematized Nomenclature of Medicine (SNOMED) terminology system.

* * * * *